United States Patent
Lee et al.

(10) Patent No.: US 10,109,805 B2
(45) Date of Patent: Oct. 23, 2018

(54) ORGANIC-INORGANIC HYBRID PEROVSKITE NANOCRYSTAL PARTICLE LIGHT EMITTING BODY HAVING TWO-DIMENSIONAL STRUCTURE, METHOD FOR PRODUCING SAME, AND LIGHT EMITTING DEVICE USING SAME

(71) Applicant: POSTECH ACADEMY-INDUSTRY FOUNDATION, Pohang-si, Gyeongsangbuk-do (KR)

(72) Inventors: Tae-Woo Lee, Pohang-si (KR); Sanghyuk Im, Hwaseong-si (KR); Young-Hoon Kim, Daegeon (KR); Himchan Cho, Daegu (KR)

(73) Assignee: POSTECH ACADEMY-INDUSTRY FOUNDATION, Pohang-si (KR)

(*) Notice: Subject to any disclaimer, the term of this patent is extended or adjusted under 35 U.S.C. 154(b) by 0 days.

(21) Appl. No.: 15/524,429

(22) PCT Filed: Nov. 6, 2015

(86) PCT No.: PCT/KR2015/011958
§ 371 (c)(1),
(2) Date: Jul. 26, 2017

(87) PCT Pub. No.: WO2016/072804
PCT Pub. Date: May 12, 2016

(65) Prior Publication Data
US 2017/0358758 A1    Dec. 14, 2017

(30) Foreign Application Priority Data
Nov. 6, 2014    (KR) .................. 10-2014-0153972

(51) Int. Cl.
*H01L 51/00*    (2006.01)
*C07F 7/24*    (2006.01)
(Continued)

(52) U.S. Cl.
CPC ............ *H01L 51/0077* (2013.01); *C07F 7/24* (2013.01); *C09K 11/06* (2013.01); *B82Y 20/00* (2013.01);
(Continued)

(58) Field of Classification Search
CPC ....... H01L 51/0077; C07F 7/24; C09K 11/06; B82Y 20/00
(Continued)

(56) References Cited

U.S. PATENT DOCUMENTS
2004/0095658 A1    5/2004    Buretea et al.

FOREIGN PATENT DOCUMENTS
JP    2001-060497    3/2001
JP    2003-309308    10/2003
KR    10-2001-0015084    2/2001

OTHER PUBLICATIONS

Mitzi. D. B. et al., "Organic-Inorganic Electronics", IBM Journal of Research and Development, Jan. 2001, vol. 45. No. 1, pp. 29-45.
(Continued)

*Primary Examiner* — Mohsen Ahmadi
*Assistant Examiner* — Patricia Reddington
(74) *Attorney, Agent, or Firm* — Lex IP Meister, PLLC

(57) ABSTRACT

Provided are an organic-inorganic-hybrid perovskite nanocrystal particle light-emitter having a two-dimensional structure, a method for producing the same, and a light emitting device using the same. The organic-inorganic-hybrid perovskite nanocrystal particle light-emitter having a two-dimensional structure comprises an organic-inorganic-hybrid perovskite nanocrystal structure having a two-dimensional structure which can be dispersed in an organic solvent. Accordingly, the nanocrystal particle light-emitter comprises an organic-inorganic-hybrid perovskite nanocrystal having a crystal structure combining FCC and BCC;
(Continued)

forms a lamellar structure where organic planes and inorganic planes are accumulated in an alternating manner; and can exhibit high color purity by confining excitons in the inorganic planes. In addition, since the exciton diffusion distance decreases and exciton binding energy increases, it is possible to prevent exciton annihilation caused by thermal ionization and delocalization of charge carriers, such that the nanocrystal particle light-emitter can have high luminescence efficiency at room temperature.

19 Claims, 3 Drawing Sheets

(51) Int. Cl.
*C09K 11/06* (2006.01)
*B82Y 20/00* (2011.01)
*B82Y 40/00* (2011.01)
*H01L 51/50* (2006.01)

(52) U.S. Cl.
CPC ........... *B82Y 40/00* (2013.01); *C09K 2211/10* (2013.01); *C09K 2211/188* (2013.01); *H01L 51/0003* (2013.01); *H01L 51/0021* (2013.01); *H01L 51/5012* (2013.01); *Y10S 977/788* (2013.01); *Y10S 977/896* (2013.01); *Y10S 977/95* (2013.01)

(58) Field of Classification Search
USPC .......................................................... 257/40
See application file for complete search history.

(56) References Cited

OTHER PUBLICATIONS

KIPO, International Search Report, Application No. of PCT/KR2015/011958, dated Mar. 21, 2016.

ORGANIC-INORGANIC HYBRID PEROVSKITE NANOCRYSTAL PARTICLE LIGHT EMITTING BODY HAVING TWO-DIMENSIONAL STRUCTURE, METHOD FOR PRODUCING SAME, AND LIGHT EMITTING DEVICE USING SAME

TECHNICAL FIELD

The present invention relates to light-emitters and their light emitting device, and more particularly, to an organic-inorganic-hybrid perovskite nanocrystal particle light-emitter and a light emitting device using the same.

BACKGROUND ART

The major trend of the display market is shifting from the existing high-efficiency and high-resolution-oriented display to the emotional image-quality display aiming at realizing a high color purity for demonstration of natural colors. In this respect, while organic light-emitter-based organic light emitting diode (OLED) devices using organic light-emitters have remarkably developed, inorganic quantum dot LEDs with the improved color purity have been actively researched and developed as alternatives. However, in the viewpoint of emitting materials, both the organic light-emitters and the inorganic quantum dot light-emitters have intrinsic limitations.

The existing organic light-emitters have an advantage of high efficiency, but the existing organic light-emitters have a wide spectrum and poor color purity. Although the inorganic quantum dot light-emitters have been known to have good color purity because the luminescence occurs by quantum size effects, there is a problem that it is difficult to uniformly control the sizes of the quantum dots as the color approaches the blue color, and thereby the size distribution deteriorates the color purity. Furthermore, because the inorganic quantum dots have a very deep valence band, there is a problem that it is difficult to inject holes because a hole injection barrier from an organic hole injection layer or an anode is too large. Also, both the light-emitters (organic emitter and inorganic quantum dot emitters) are disadvantageously expensive. Thus, there is a need for new types of hybrid organic-inorganic light-emitters that compensate for the disadvantages of the organic light-emitters and inorganic quantum dot emitters and maintains their merits.

Since the emitting materials based on hybrid of organic and inorganic materials (hereafter, organic-inorganic-hybrid) have advantages of low manufacturing costs and simple manufacturing and device manufacturing processes and also have all advantages of organic emitting materials, which are easy to control optical and electrical properties, and inorganic emitting materials having high charge mobility and mechanical and thermal stability, the organic-inorganic-hybrid emitting materials are attracting attention academically and industrially.

Among them, since the organic-inorganic-hybrid perovskite materials have high color purity, simple color control, and low synthesis costs, the organic-inorganic-hybrid perovskite materials are very likely to be developed as the light-emitters. The high color purity (full width at half maximum (FWHM)≈20 nm) from these materials can be realized because they have a layered structure in which a two-dimensional (2D) plane made of the inorganic material is sandwiched between 2D planes made of the organic material and a large difference in dielectric constant between the inorganic material and the organic material is large ($\varepsilon_{organic} \approx 2.4$, $\varepsilon_{inorganic} \approx 6.1$) so that the electron-hole pairs (or excitons) are bound to the inorganic 2D layer.

An organic-inorganic-hybrid metal halide perovskite having a perovskite crystal structure is currently being studied mainly as a light absorber of a solar cell, but its characteristics have also very large possibility as a light-emitter. Since the organic-inorganic-hybrid perovskite has a structure in which the organic plane (i.e. "A site cation" plane in the perovskite crystal structure) and the inorganic plane are alternately laminated and thus has a lamellar structure so that the excitons are bound in the inorganic plane, it may be an ideal luminescent material that generally emits light having very high purity by the intrinsic crystal structure itself rather than the quantum size effect of the material.

For example, although an electroluminescent device in which a emitting dye-containing organic-inorganic-hybrid material is formed in the form of a thin film and used as a light emitting layer, the emission originated from the emitting-dye itself, not the intrinsic crystal structure as disclosed in Korean Patent Publication No. 10-2001-0015084 (Feb. 26, 2001).

However, since the organic-inorganic-hybrid perovskite has small exciton binding energy, there is a fundamental problem that the luminescence occurs at a low temperature, but the excitons do not emit light at room temperature due to thermal ionization and delocalization of a charge carrier and thus they are easily separated as free charge carriers and then annihilated. Also, there is a problem in which the excitons are annihilated by the layer having high conductivity in the vicinity of the excitons after the free charge carriers are recombined to form excitons. Therefore, to improve luminescence efficiency and brightness of the organic-inorganic-hybrid perovskite-based LED, it is necessary to prevent the exitons from being quenched.

DISCLOSURE OF THE INVENTION

Technical Problem

To solve the abovementioned problems, the present invention provides a nanocrystal particles light-emitter having improved luminescence efficiency and durability (or stability) by synthesizing organic-inorganic-hybrid perovskite particles having a two-dimensional structure into nanocrystal instead of forming a polycrystal thin film in order to prevent thermal ionization, delocalization of charge carriers, and quenching of excitons, and light emitting device using the same.

Technical Solution

To achieve the objectives, one aspect of the present invention provides an organic-inorganic-hybrid perovskite nanocrystal particle light-emitter, which has a two-dimensional structure. The organic-inorganic-hybrid perovskite nanocrystal particle light-emitter, which has a two-dimensional structure, includes an organic-inorganic-hybrid hybrid perovskite nanocrystal structure, which is capable of being dispersible in an organic solvent and has a two-dimensional structure.

The organic solvent may include a polar solvent and a non-polar solvent, the polar solvent may include dimethylformamide, gamma butyrolactone, N-methylpyrrolidone, dimethylsulfoxide or isopropyl alcohol, and the non-polar solvent may include dichloroethylene, trichlorethylene, chloroform, chlorobenzene, dichlorobenzene, styrene, xylene, toluene, or cyclohexene.

Here, the 2D structure may be an organic-inorganic-hybrid perovskite nanocrystal structure with a center metal centered in a face centered cubic, in which six inorganic halide materials X are respectively located on all surfaces of a hexahedron, and in a body centered cubic, in which eight organic or inorganic ammonium are respectively located at all vertexes of a hexahedron and is defined as a structure of which a horizontal length and a vertical length are the same, but a height length is longer by 1.5 times or more than each of the horizontal length and the vertical length.

Here, the nanocrystal particle may have a spherical, cylindrical, cylindroid, polyprism, or two-dimensional (lamellar, plate) shape. Also, the nanocrystal particle may have a size of 1 nm to 900 nm.

The nanocrystal particle light-emitter may have an emission wavelength of 200 nm to 1300 nm.

Also, the organic-inorganic-hybrid perovskite nanocrystal particle may have bandgap energy determined by the intrinsic crystal structure without depending on the particle size.

Also, the nanocrystal particle may have bandgap energy of 1 eV to 5 eV.

The organic-inorganic-hybrid metal halide perovskite may have a structure of $A_2BX_4$, $ABX_4$, or $A_{n-1}B_nX_{3n+1}$ (where n is an integer between 2 to 6), and the A may be organic ammonium, the B may be a metal material, the X may be a halogen element. The A may be $(CH_3NH_3)_n$, $((C_xH_{2x+1})_nNH_3)_2$ $(CH_3NH_3)_n$, $(RNH_3)_2$, $(C_nH_{2n+1}NH_3)_2$, $CF_3NH_3$, $(CF_3NH_3)_n$, $((C_xF_{2x+1})_nNH_3)_2$ $(CF_3NH_3)_n$, $((C_xF_{2x+1})_nNH_3)_2$, $(C_nF_{2n+1}NH_3)_2$, $(CH(NH_2)_2)$, $C_xH_{2x+1}(C(NH_2)_2)$, Cs, Rb, K, or a combination thereof (where n is an integer equal to or greater than 1, and x is an integer equal to or greater than 1), the B may be a divalent transition metal, a rare earth metal, an alkali earth metal, Pb, Sn, Ge, Ga, In, Al, Sb, Bi, Po, or a combination thereof, and the X may be Cl, Br, I, or a combination thereof.

Also, the organic-inorganic-hybrid perovskite nanocrystal particle light-emitter may further include a plurality of organic ligands surrounding a surface of the organic-inorganic-hybrid perovskite nanocrystal particle. Each of the organic ligands may have a 2D structure including alkyl halide. An alkyl structure of the alkyl halide may include acyclic alkyl having a structure of $C_nH_{2n+1}$, primary alcohol, secondary alcohol, tertiary alcohol, alkylamine, p-substituted aniline, phenyl ammonium, or fluorine ammonium.

To achieve the objects, another aspect of the present invention provides a method for manufacturing an organic-inorganic-hybrid perovskite nanocrystal particle light-emitter having a 2D structure. The method for manufacturing an organic-inorganic-hybrid perovskite nanocrystal particle light-emitter having a 2D structure includes steps of: preparing a first solution in which organic-inorganic-hybrid perovskite having a 2D structure is dissolved in a polar solvent and a second solution in which an alkyl halide surfactant is dissolved in anon-polar solvent; and mixing the first solution with the second solution to form the nanocrystal particle.

Also, the step of mixing the first solution with the second solution may include a step of dropping the first solution dropwise into the second solution to mix the first and second solutions with each other.

Also, the organic-inorganic-hybrid perovskite may have a structure of $A_2BX_4$, $ABX_4$, or $A_{n-1}BnX_{3n+1}$ (where n is an integer between 2 to 6), and the A may be organic ammonium, the B may be a metal material, the X may be a halogen element. The A may be $(CH_3NH_3)_n$, $((C_xH_{2x+1})_nNH_3)_2$ $(CH_3NH_3)_n$, $(RNH_3)_2$, $(C_nH_{2n+1}NH_3)_2$, $CF_3NH_3$, $(CF_3NH_3)_n$, $((C_xF_{2x+1})_nNH_3)_2$ $(CF_3NH_3)_n$, $((C_xF_{2x+1})_n$ $NH_3)_2$, $(C_nF_{2n+1}NH_3)_2$, $(CH(NH_2)_2)$, $C_xH_{2x+1}(C(NH_2)_2)$, Cs, Rb, K, or a combination thereof (where n is an integer equal to or greater than 1, and x is an integer equal to or greater than 1), the B may be a divalent transition metal, a rare earth metal, an alkali earth metal, Pb, Sn, Ge, Ga, In, Al, Sb, Bi, Po, or a combination thereof, and the X may be Cl, Br, I, or a combination thereof.

Also, the first solution may be formed by mixing AX and $BX_2$ with the polar solvent at a predetermined ratio.

To achieve the objectives, further another aspect of the present invention provides a light emitting device. The light emitting device includes: a first electrode; a second electrode; and a light emitting layer disposed between the first electrode and the second electrode and haves the abovementioned organic-inorganic-hybrid perovskite nanocrystal particle light-emitter.

Advantageous Effects

In the nanocrystal particle light-emitters that have the 2D organic-inorganic-hybrid perovskite, the organic-inorganic-hybrid perovskite nanocrystal having the crystal structure, in which the FCC and the BCC are combined with each other, may be formed in the nanocrystal particle light-emitter to form a lamellar structure in which the organic plane and the inorganic plane are alternately stacked, and also, the excitons may be confined in the inorganic plane to implement the high color purity.

Also, the exciton diffusion length may be reduced, and the exciton binding energy may increase in the nanocrystal particle having a size of 900 nm or less to prevent the excitons from being annihilated by thermal ionization and the delocalization of the charge carriers, thereby improving the luminescence efficiency at room temperature.

Also, the bandgap energy of the organic-inorganic-hybrid perovskite nanocrystal particle may be determined by the crystal structure without depending on the particle size.

Furthermore, when compared to the organic-inorganic-hybrid perovskite having the 3D structure such as the $ABX_3$ structure, the organic-inorganic-hybrid perovskite nanocrystal having the 2D structure such as the $A_2BX_4$, $ABX_4$, $A_{n-1}BnX_{3n+1}$ structure may be synthesized to increase the distance between the inorganic planes confined in the excitons, resulting in increasing in the exciton binding energy, thereby improving the luminescence efficiency and the durability (or stability).

Also, according to the method for manufacturing the organic-inorganic-hybrid perovskite nanocrystal particle light-emitter according to the present invention, the size of organic-inorganic-hybrid perovskite nanocrystal particle light-emitter is adjusted according to the length and size of the alkyl halide surfactant.

The effects of the present invention are not limited to the aforementioned effects, but other objects not described herein will be clearly understood by those skilled in the art from descriptions below.

MODE FOR CARRYING OUT THE INVENTION

Hereinafter, embodiments of the present invention will be described in detail with reference to the accompanying drawings.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

In the following description, it will be understood that when an element such as a layer, a region, or substrate is referred to as being 'on' another layer, region, or substrate, it can be directly on the other layer, region, or substrate, or intervening layers, regions, or substrates may also be present.

Although the terms such as "first," "second," etc., are used to describe various element, components, regions, layers, and/or portions, it is obvious that the elements, components, regions, layers, and/or portions should not be defined by these terms.

Figure 1:
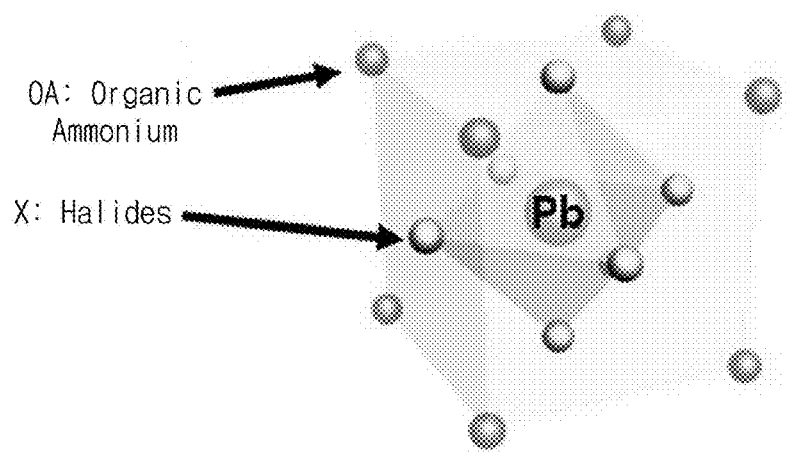
FIG. 1 is a schematic view of a perovskite nanocrystal structure according to an embodiment of the present invention.

FIG. 1 is a schematic view of an organic-inorganic-hybrid perovskite nanocrystal structure according to an embodiment of the present invention.

Referring to FIG. 1, the organic-inorganic-hybrid perovskite nanocrystal has a structure with a center metal centered in a face centered cubic (FCC), in which six inorganic halide materials X are respectively located on all surfaces of a hexahedron, and in a body centered cubic (BCC), in which eight organic ammonium OA or inorganic cation are respectively located at all vertexes of a hexahedron. Here, Pb is illustrated as an example of the center metal.

Here, all sides of the hexahedron have an angle of 90° with respect to each other. The above-described structure may include a cubic structure having the same length in horizontal, vertical, and height directions and a tetragonal structure having different lengths in the horizontal, vertical, and height directions.

Thus, the two-dimensional (2D) structure according to the present invention may be the organic-inorganic-hybrid perovskite nanocrystal structure with a center metal centered in a face centered cubic, in which six inorganic halide materials X are respectively located on all surfaces of a hexahedron, and in a body centered cubic, in which eight organic ammonium or inorganic cations are respectively located at all vertexes of a hexahedron and be defined as a structure of which a horizontal length and a vertical length are the same, but a height length is longer by 1.5 times or more than each of the horizontal length and the vertical length.

A method for manufacturing the organic-inorganic-hybrid perovskite nanocrystal colloidal particle light-emitter having the 2D structure according to an embodiment of the present invention will be described.

Figure 2:
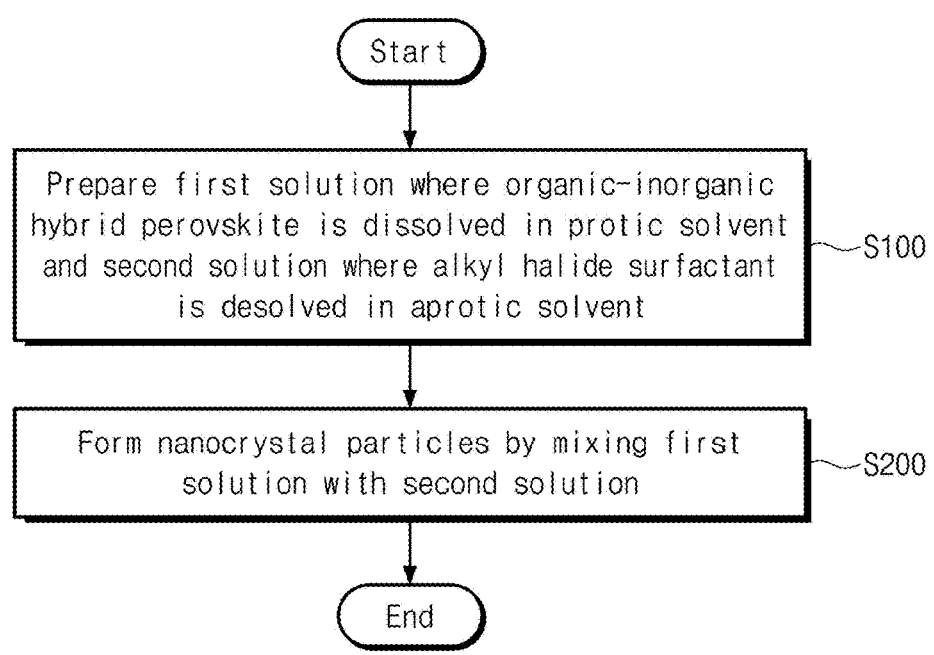
FIG. 2 is a flowchart illustrating a method for manufacturing the organic-inorganic-hybrid perovskite nanocrystal colloidal particle light-emitter having a 2D structure according to an embodiment of the present invention.

FIG. 2 is a flowchart illustrating a method for manufacturing the organic-inorganic-hybrid perovskite nanocrystal particle light-emitter having a 2D structure according to an embodiment of the present invention.

Referring to FIG. 2, a method for manufacturing the organic-inorganic-hybrid perovskite nanocrystal particle according to an embodiment of the present invention may include a step (S100) of preparing a first solution in which organic-inorganic-hybrid perovskite having the 2D structure is dissolved in a polar solvent and a second solution in which an alkyl halide surfactant is dissolved in an non-polar solvent and a step of mixing the first solution with the second solution to form nanocrystalline particles.

That is, the organic-inorganic-hybrid perovskite nanocrystalline particle light-emitter having the 2D structure according to the present invention may be manufactured through an inverse nano-emulsion method, reprecipitation method or hot-injection method.

Hereinafter, more specifically,

First, the first solution in which the organic-inorganic-hybrid perovskite having the 2D structure is dissolved in a polar solvent and the second solution in which a surfactant is dissolved in a non-polar solvent are prepared (S110).

Here, the polar solvent may include dimethylformamide, gamma butyrolactone, N-methylpyrrolidone, dimethylsulfoxide or iso-propyl alcohol but is not limited thereto.

Also, the organic-inorganic-hybrid perovskite may be a material having the two-dimensional crystalline structure. For example, the organic-inorganic-hybrid perovskite may be a structure of $A_2BX_4$, $ABX_4$, $A_{n-1}Pb_nX_{3n+1}$ (where, n is an integer between 2 to 6).

Here, the A is an organic ammonium material, the B is a metal material, and the X is a halogen element.

For example, the A may be $(CH_3NH_3)_n$, $((C_xH_{2x+1})_nNH_3)_2$, $(CH_3NH_3)_n$, $(RNH_3)_2$, $(C_nH_{2n+1}NH_3)_2$, $CF_3NH_3$, $(CF_3NH_3)_n$, $((C_xF_{2x+1})_nNH_3)_2$, $(CF_3NH_3)_n$, $((C_xF_{2x+1})_nNH_3)_2$, $(CH(NH_2)_2)$, $C_xH_{2x+1}(C(NH_2)_2)$, Cs, Rb, K or $(C_nF_{2n+1}NH_3)_2$ or a combination thereof (where n is an integer equal to or greater than 1, and x is an integer equal to or greater than 1). Here, the B may be a divalent transition metal, a rare earth metal, an alkali earth metal, Pb, Sn, Ge, Ga, In, Al, Sb, Bi, Po, or a combination thereof. The X may be Cl, Br, I, or a combination thereof.

The perovskite may be prepared by combining the AX with $BX_2$ at a predetermined ratio. That is, the first solution may be formed by dissolving the AX and $BX_2$ in the polar solvent at a predetermined ratio. For example, the AX and $BX_2$ may be dissolved in the polar solvent at a ratio of 2:1 to prepare the first solution in which the $A_2BX_3$ organic-inorganic-hybrid perovskite is dissolved.

Also, the polar solvent may include dimethylformamide, gamma butyrolactone, N-methylpyrrolidone, dimethylsulfoxide or isopropyl alcohol but is not limited thereto.

Also, the alkyl halide surfactant may have a structure of alkyl-X. Here, the halogen element corresponding to the X may include Cl, Br, or I. Also, the alkyl structure may include acyclic alkyl having a structure of $C_nH_{2n+1}$, primary alcohol having a structure such as $C_nH_{2n+1}OH$, secondary alcohol, tertiary alcohol, alkylamine having a structure of alkyl-N (e.g., hexadecyl amine, 9-Octadecenylamine 1-Amino-9-octadecene ($C_{19}H_{37}N$)), p-substituted aniline, phenyl ammonium, or fluorine ammonium, but is not limited thereto.

Next, the first solution may be mixed with the second solution to form the nanocrystal particle. (S200).

In the step of mixing the first solution with the second solution to form the nanocrystal particle, it is preferable to mix the first solution by dropping into the second solution in drops. Also, the second solution may be stirred. For example, the first solution in which the organic-inorganic-hybrid perovskite (OIP) is dissolved may be slowly added dropwise into the second solution in which the alkyl halide surfactant that is strongly stirred is dissolved to synthesize the nanocrystal particle.

In this case, when the first solution drops are mixed with the second solution, the organic-inorganic-hybrid perovskite (OIP) is precipitated from the second solution due to a difference in solubility. Also, the organic-inorganic-hybrid perovskite (OIP) precipitated from the second solution generates an organic-inorganic-hybrid perovskite nanocrystal (alp-NC) that is well dispersed while stabilizing a surface thereof by the alkyl halide surfactant. Thus, the organic-inorganic-hybrid perovskite nanocrystal particle light-emitters that have the organic-inorganic-hybrid perovskite nanocrystal structure or inorganic metal halide perovskite nanocrystal and the plurality of organic ligands or inorganic binary compounds surrounding the organic-inorganic-hybrid perovskite nanocrystal structure may be manufactured.

The organic-inorganic-hybrid perovskite nanocrystal particle may have a size that is controllable by adjusting a length or a shape of the alkyl halide surfactant. For example, the adjustment of the shape may be controlled through the surfactant having a linear, tapered, or inverted triangular shape.

It is preferable that the generated organic-inorganic-hybrid perovskite nanocrystal particle has a size of 1 nm to 900 nm. Here, the size of the nanocrystal particle represents a size without considering a size of the ligand that will be described later, i.e., a size of a remaining portion except for the ligand.

If the organic-inorganic-hybrid perovskite nanocrystal has a size exceeding 900 nm, it is a fundamental problem in which the light emission of the exciton at room temperature does not occur efficiently by the thermal ionization and the delocalization of the charge carrier, and the exciton is separated as free charge carriers and then annihilated.

Figure 3:
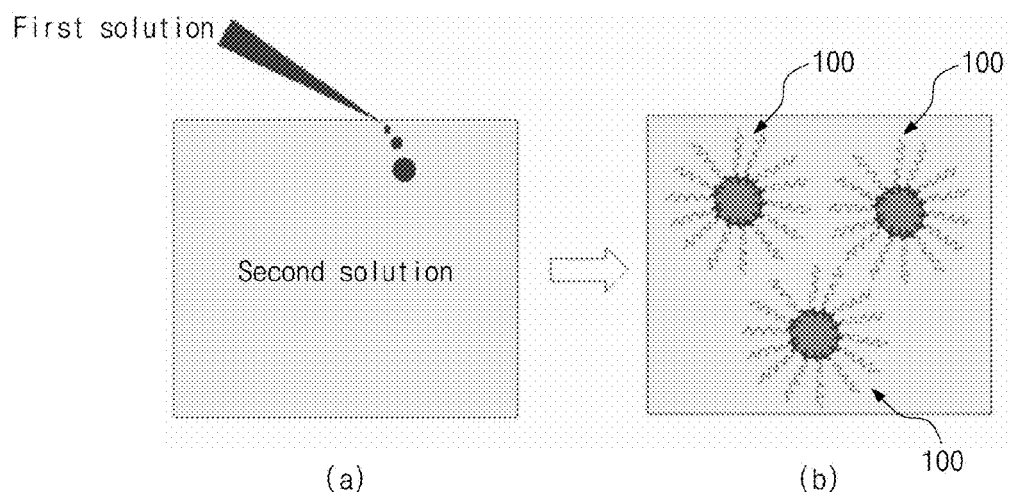
FIG. 3 is a schematic view illustrating a method for manufacturing the organic-inorganic-hybrid perovskite nanocrystal colloidal particle light-emitter having the 2D structure according to an embodiment of the present invention.

FIG. 3 is a schematic view illustrating a method for manufacturing the organic-inorganic-hybrid perovskite nanocrystal particle light-emitter having the 2D structure through the inverse nano-emulsion method according to an embodiment of the present invention.

Referring to FIG. 3(a), the first solution in which the organic-inorganic-hybrid perovskite having the 2D structure is dissolved in the polar solvent is added into the second solution in which the alkyl halide surfactant is dissolved in the non-polar solvent.

Here, the polar solvent may include dimethylformamide, gamma butyrolactone, N-methylpyrrolidone, dimethylsulfoxide or isopropyl alcohol, but is not limited thereto.

Here, the organic-inorganic-hybrid perovskite having the 2D crystal structure may be a structure of $A_2BX_4$, $ABX_4$, or $A_{n-1}B_nX_{3n+1}$ (where, n is an integer between 2 to 6). Here, the A is an organic ammonium material, the B is a metal material, and the X is a halogen element. For example, the A may be $(CH_3NH_3)_n$, $((C_xG_{2x+1})_nNH_3)_2$ $(CH_3NH_3)_n$, $(RNH_3)_2$, $(C_nH_{2n+1}NH_3)_2$, $CF_3NH_3$, $(CF_3NH_3)_n$, $((C_xF_{2x+1})_nNH_3)_2$ $(CF_3NH_3)_n$, $((C_xF_{2x+1})_nNH_3)_2$, $(CH(NH_2)_2)$, $C_xH_{2x+1}$ $(C(NH_2)_2)$, Cs, Rb, K, $(C_nH_{2n+1}NH_3)_2$ or combination of thereof (where n is an integer equal to or greater than 1, and x is an integer equal to or greater than 1).

Here, the B may be a divalent transition metal, a rare earth metal, an alkali earth metal, Pb, Sn, Ge, Ga, In, Al, Sb, Bi, Po, or a combination thereof. Here, the rare earth metal may be, for example, Ge, Sn, Pb, Eu, or Yb. Also, the alkali earth metal may be, for example, Ca or Sr. Also, the X may be Cl, Br, I, or a combination thereof.

The perovskite structure may be formed through a combination of AX and $BX_2$ with different $AX:BX_2$ ratios. For example, the AX and $BX_2$ may be dissolved in the polar solvent at a ratio of 2:1 to prepare the first solution in which the $A_2BX_4$ organic-inorganic-hybrid perovskite is dissolved.

When the A is $CH_3NH_3$, and the X is Br as an example of the AX synthesis, $CH_3NH_2$ (methylamine) and HBr (hydroiodic acid) may be dissolved under a nitrogen atmosphere to obtain $CH_3NH_3Br$ through evaporation of the solvent.

Referring to FIG. 3(b), when the first solution is added to the second solution, the organic-inorganic-hybrid perovskite is precipitated from the second solution due to a difference in solubility. A surface of the precipitated organic-inorganic-hybrid perovskite is surrounded by the alkyl halide surfactant and thus stabilized to generate an organic-inorganic-hybrid perovskite nanocrystal particle light-emitters 100 that have the organic-inorganic-hybrid perovskite nanocrystal structure that is well dispersed. Here, the surface of the organic-inorganic-hybrid perovskite nanocrystal particle is surrounded by the organic ligands that are alkyl halide, polymers, organic small molecules, inorganic binary compounds or combination thereof.

Thereafter, the solution including the organic-inorganic-hybrid perovskite nanocrystal particle light-emitter 100 that is dispersed in the non-polar solvent, in which the alkyl halide surfactant is dissolved, may be heated and thus selectively evaporated, or a co-solvent, in which all the polar and non-polar solvents are capable of being dissolved, may be added to selectively extract the polar solvent including the nanocrystal particle from the non-polar solvent, thereby obtaining the organic-inorganic-hybrid perovskite nanocrystal particle light-emitter.

The organic-inorganic-hybrid perovskite nanocrystal particle light-emitter having the 2D structure according to an embodiment of the present invention will be described.

The organic-inorganic-hybrid perovskite nanocrystal colloidal particle light-emitter according to an embodiment of the present invention may include an organic-inorganic-hybrid perovskite nanocrystal structure that has the 2D structure and is dispersible in an organic solvent. Here, the organic solvent may be the polar solvent or the non-polar solvent. For example, the polar (aprotic or protic) solvent may include dimethylformamide, gamma butyrolactone, N-methylpyrrolidone, dimethylsulfoxide or isopropyl alcohol, and the non-polar solvent may include dichloroethylene, trichlorethylene, chloroform, chlorobenzene, dichlorobenzene, styrene, xylene, toluene, or cyclohexene.

Also, the nanocrystal particle may have a spherical, cylindrical, cylindroid, polyprism or two-dimensional (lamellar, plate) shape.

Also, the nanocrystal particle may have a size of 1 nm to 900 nm. For example, when the nanocrystal particle has the spherical shape, the nanocrystal particle may have a diameter of 1 nm to 900 nm.

Here, the size of the nanocrystal particle represents a size without considering a size of the ligand that will be described later, i.e., a size of a remaining portion except for the ligand.

Also, the nanocrystal particle may have bandgap energy of 1 eV to 5 eV. Thus, since the energy bandgap is determined according to the composition and the crystal structure of the nanocrystal particle, the composition of the nanocrystal particle may be adjusted to emit light having a wavelength of, for example, 200 nm to 1300 nm.

Also, the plurality of organic ligands or inorganic binary compounds or combination thereof surrounding the surface of the organic-inorganic-hybrid or metal halide perovskite nanocrystal structure may be further provided.

Hereinafter, embodiments of the present invention will be described with reference to FIG. 3.

FIG. 3 is a schematic view of the organic-inorganic-hybrid perovskite nanocrystal particle light-emitter having the 2D structure according to an embodiment of the present invention.

Figure 4:
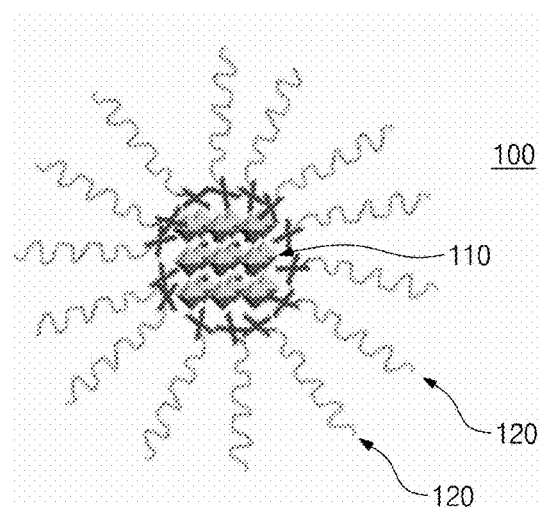
FIG. 4 is a schematic view of the organic-inorganic-hybrid perovskite nanocrystal colloidal particle light-emitter having the 2D structure according to an embodiment of the present invention.
Figure 5:
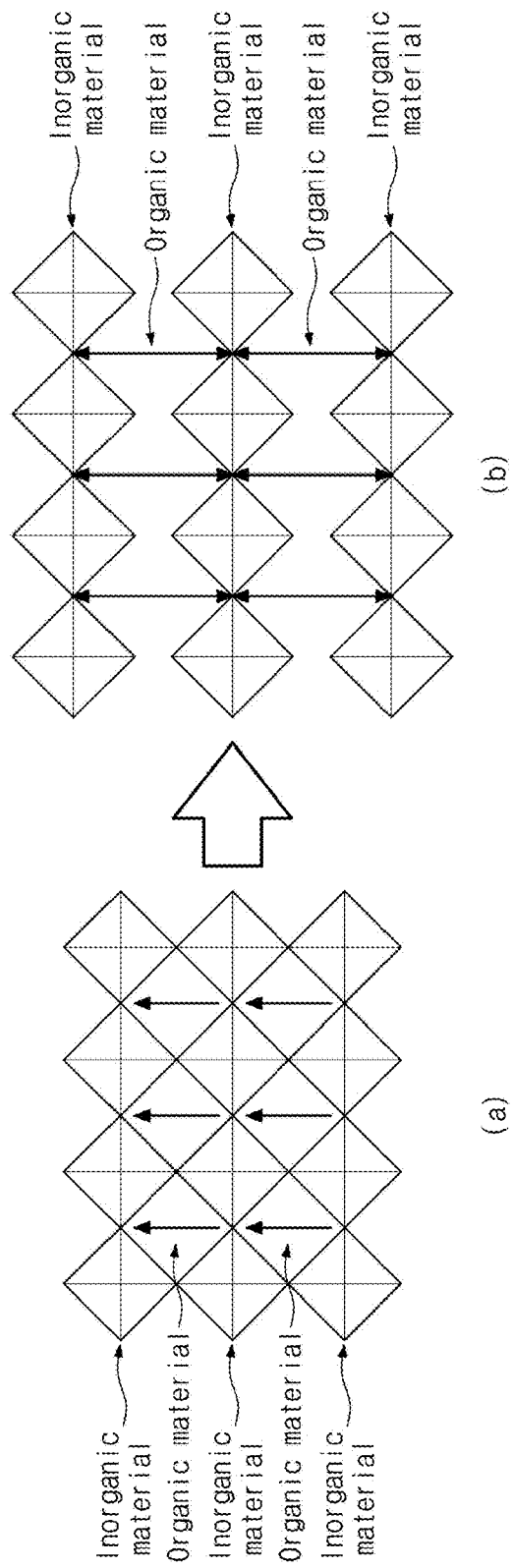
FIG. 5 is a schematic view of the organic-inorganic-hybrid perovskite nanocrystal having the 2D structure, which is manufactured through an inverse nano-emulsion method, reprecipitation method or hot-injection method according to the present invention.

Referring to FIG. 4, the light-emitter according to an embodiment of the present invention includes an organic-inorganic-hybrid perovskite nanocrystal structure 110 having a 2D structure, which has a lamellar structure in which an organic plane and an inorganic plane are alternately stacked, as an organic-inorganic-hybrid perovskite nanocrystal particle that has a 2D structure and is dispersible in an organic solvent.

The organic-inorganic-hybrid perovskite having the 2D crystal structure may be a structure of $A_2BX_4$, $ABX_4$, or $A_{n-1}Pb_nX_{3n+1}$ (where, n is an integer between 2 to 6).

Here, the A is an organic ammonium material, the B is a metal material, and the X is a halogen element. For example, the A may be $(CH_3NH_3)_n$, $((C_xH_{2x+1})_nNH_3)_2$ $(CH_3NH_3)_n$, $(RNH_3)_2$, $(C_nH_{2n+1}NH_3)_2$, $CF_3NH_3$, $(CF_3NH_3)_n$, $((C_xF_{2x+1})_nNH_3)_2$ $(CF_3NH_3)_n$, $((C_xF_{2n+1})_nNH_3)_2$, $(CH(NH_2)_2)$, $C_xH_{2x+1}(C(NH_2)_2)$, Cs, Rb, K, $(C_nF_{2n+1}NH_3)_2$ or a combination thereof (where n is an integer equal to or greater than 1, and x is an integer equal to or greater than 1). Here, the B may be a divalent transition metal, a rare earth metal, an alkali earth metal, Pb, Sn, Ge, Ga, In, Al, Sb, Bi, Po, or a combination thereof. Here, the rare earth metal may be, for example, Ge, Sn, Pb, Eu, or Yb. Also, the alkali earth metal may be, for example, Ca or Sr. Also, the X may be Cl, Br, I, or a combination thereof.

The organic-inorganic-hybrid perovskite nanocrystal particle light-emitter 100 having the 2D structure according to the present invention may further include a plurality of organic ligands 120 or inorganic binary compounds or combination thereof surrounding the above-described organic-inorganic-hybrid metal halide perovskite nanocrystal structure or inorganic metal halide perovskite nanocrystal structure 110. Each of the organic ligands 120 may be a material used as the surfactant and include alkyl halide. Thus, as described above, the alkyl halide used as the surfactant for stabilizing the surface of the precipitated organic-inorganic-hybrid perovskite may become the organic ligand surrounding the surface of the organic-inorganic-hybrid perovskite nanocrystal.

If the alkyl halide surfactant has a short length, the size of formed nanocrystal particle may increase to exceed 900 nm. In this case, the luminescence of the exciton at room temperature may not occur efficiently by thermal ionization and the delocalization of the charge carrier in the large nanocrystal, and the exciton may be separated as free charge carriers and then annihilated.

That is, the size of the formed organic-inorganic-hybrid perovskite nanocrystal particle is inversely proportional to the length of the alkyl halide surfactant used for forming the nanocrystal particle.

Thus, the size of the organic-inorganic-hybrid perovskite nanocrystal particle formed by using the alkyl halide having a predetermined length or more as the surfactant may be controlled to a predetermined size or less. For example, octadecyl-ammonium bromide may be used as the alkyl halide surfactant to form the organic-inorganic-hybrid perovskite nanocrystal particle having a size of a 900 nm or less.

A light emitting device according to an embodiment of the present invention will be described.

A light emitting device according to an embodiment of the present invention may be a device using a light emitting layer including the organic-inorganic-hybrid perovskite nanocrystal particle light-emitter having the 2D structure.

For example, the light emitting device according to the present invention may include a first electrode, a second electrode, and a light emitting layer, disposed between the first electrode and the second electrode, including the organic-inorganic-hybrid perovskite nanocrystal light-emitter.

Manufacturing Example 1

The organic-inorganic-hybrid perovskite nanocrystal particle light-emitter having the 2D structure according to an embodiment of the present invention was described. The inorganic metal halide perovskite nanocrystal particle light-emitter was formed through an inverse nano-emulsion method, reprecipitation method or hot-injection method.

Particularly, organic-inorganic-hybrid perovskite was dissolved in a polar solvent to prepare a first solution. Here, dimethylformamide was used as the polar solvent, and $(CH_3NH_3)_2PbBr_4$ was used as the organic-inorganic-hybrid perovskite. Here, the used $(CH_3NH_3)_2PbBr_4$ was prepared by mixing $CH_3NH_3Br$ with $PbBr_2$ at a ratio of 2:1.

Also, a second solution in which an alkyl halide surfactant is dissolved in a non-polar solvent was prepared. Here, toluene was used as the non-polar solvent, and octadecylammonium bromide $(CH_3(CH_2)_{17}NH_3Br)$ was used as the alkyl halide surfactant.

Then, the first solution dropwise dropped into the second solution that is being strongly stirred to form a nanocrystal particle light-emitters that have an organic-inorganic-hybrid perovskite nanocrystal particle light-emitter having a 2D structure.

Here, the organic-inorganic-hybrid perovskite nanocrystal particle has a size of about 20 nm.

Then, the organic-inorganic-hybrid perovskite nanocrystal particle that is in a liquid state was spin-coated on a glass substrate to form an organic-inorganic-hybrid perovskite nanocrystal particle thin film (OIP-NP film).

Here, the formed organic-inorganic-hybrid perovskite nanocrystal particle has a size of about 20 nm.

Manufacturing Example 2

The same process according to Manufacturing Example 1 was performed, and $CH_3(CH_2)_{13}NH_3Br$ was used as an alkyl halide surfactant to form an organic-inorganic-hybrid perovskite nanocrystal particle light-emitter having a 2D structure according to an embodiment of the present invention.

Here, the formed organic-inorganic-hybrid perovskite nanocrystal particle has a size of about 100 nm.

Manufacturing Example 3

The same process according to Manufacturing Example 1 was performed, and $CH_3(CH_2)_{10}NH_3Br$ was used as an alkyl halide surfactant to form an organic-inorganic-hybrid perovskite nanocrystal particle light-emitter having a 2D structure according to an embodiment of the present invention.

Here, the formed organic-inorganic-hybrid perovskite nanocrystal particle has a size of about 300 nm.

Manufacturing Example 4

The same process according to Manufacturing Example 1 was performed, and $CH_3(CH_2)_7NH_3Br$ was used as an alkyl halide surfactant to form an organic-inorganic-hybrid perovskite nanocrystal particle light-emitter having a 2D structure according to an embodiment of the present invention.

Here, the formed organic-inorganic-hybrid perovskite nanocrystal particle has a size of about 500 nm.

Manufacturing Example 5

The same process according to Manufacturing Example 1 was performed, and $CH_3(CH_2)_4NH_3Br$ was used as an alkyl halide surfactant to form an organic-inorganic-hybrid perovskite nanocrystal particle light-emitter having a 2D structure according to an embodiment of the present invention.

Here, the formed organic-inorganic-hybrid perovskite nanocrystal particle has a size of about 700 nm.

Manufacturing Example 6

The same process according to Manufacturing Example 1 was performed, and $CH_3CH_2NH_3Br$ was used as an alkyl halide surfactant to form an organic-inorganic-hybrid perovskite nanocrystal particle light-emitter having a 2D structure according to an embodiment of the present invention.

Here, the formed organic-inorganic-hybrid perovskite nanocrystal particle has a size of about 800 nm.

Manufacturing Example 7

The same process according to Manufacturing Example 1 was performed, and $CH_3NH_3Br$ was used as an alkyl halide surfactant to form an organic-inorganic-hybrid perovskite nanocrystal particle light-emitter having a 2D structure according to an embodiment of the present invention.

Here, the formed organic-inorganic-hybrid perovskite nanocrystal particle has a size of about 900 nm.

Manufacturing Example 8

The same process according to Manufacturing Example 1 was performed, and $(CH_3NH_3)_2PbCl_4$ was used as the organic-inorganic-hybrid perovskite. Here, the used $(CH_3NH_3)_2PbCl_4$ was prepared by mixing $CH_3NH_3Cl$ with $PbCl_2$ at a ratio of 2:1.

Here, the formed organic-inorganic-hybrid perovskite nanocrystalline particle emits light near to ultraviolet or blue color. The luminescence spectrum is located at about 380 nm.

Manufacturing Example 9

The same process according to Manufacturing Example 1 was performed, and $(CH_3NH_3)_2PbI_4$ was used as the organic-inorganic-hybrid perovskite. Here, the used $(CH_3NH_3)_2PbI_4$ was prepared by mixing $CH_3NH_3I$ with $PbI2$ at a ratio of 2:1.

Here, the formed organic-inorganic-hybrid perovskite nanocrystalline particle emits light near to infrared or red color. The luminescence spectrum is located at about 780 nm.

Manufacturing Example 10

The same process according to Manufacturing Example 1 was performed, and $(CH_3NH_3)_2PbCl_xBr_{4-x}$ was used as the organic-inorganic-hybrid perovskite. Here, the used $(CH_3NH_3)_2PbCl_xBr_{4-x}$ was prepared by mixing $CH_3NH_3Cl$ with $PbBr_2$ at a ratio of 2:1.

Here, the luminescence spectrum of the formed organic-inorganic-hybrid perovskite nanocrystalline particle is located between 380 nm and 520 nm.

Manufacturing Example 11

The same process according to Manufacturing Example 1 was performed, and $(CH_3NH_3)_2PbI_xBr_{4-x}$ was used as the organic-inorganic-hybrid perovskite. Here, the used $(CH_3NH_3)_2PbI_xBr_{4-x}$ was prepared by mixing $CH_3NH_3I$ with $PbBr_2$ at a predetermined ratio.

Here, the luminescence spectrum of the formed organic-inorganic-hybrid perovskite nanocrystalline particle is located between 520 nm and 780 nm.

Manufacturing Example 12

The same process according to Manufacturing Example 1 was performed, and $(CH(NH_2)_2)_2PbI_4$ was used as the organic-inorganic-hybrid perovskite. Here, the used $(CH(NH_2)_2)_2PbI_4$ was prepared by mixing $CH(NH2)_2I$ with $PbI_2$ at a ratio of 2:1.

Here, the luminescence spectrum of the formed organic-inorganic-hybrid perovskite nanocrystalline particle emits infrared light and is located at about 800 nm.

Manufacturing Example 13

The same process according to Manufacturing Example 1 was performed, and $(CH_3NH_3)_2Pb_xSn_{1-x}I_4$ was used as the organic-inorganic-hybrid perovskite. Here, the used $(CH_3NH_3)_2Pb_xSn_{1-x}I_4$ was prepared by mixing $CH_3NH_3I$ with $Pb_xSn_{1-x}I_2$ at a ratio of 2:1.

Here, the luminescence spectrum of the formed organic-inorganic-hybrid perovskite nanocrystalline particle is located between 820 nm and 1120 nm.

Manufacturing Example 14

The same process according to Manufacturing Example 1 was performed, and $(CH_3NH_3)_2Pb_xSn_{1-x}Br_4$ was used as the organic-inorganic-hybrid perovskite. Here, the used $(CH_3NH_3)_2Pb_xSn_{1-x}Br_4$ was prepared by mixing $CH_3NH_3Br$ with $Pb_xSn_{1-x}Br_2$ at a ratio of 2:1.

Here, the luminescence spectrum of the formed organic-inorganic-hybrid perovskite nanocrystalline particle is located between 540 nm and 650 nm.

Manufacturing Example 15

The same process according to Manufacturing Example 1 was performed, and $(CH_3NH_3)_2Pb_xSn_{1-x}Cl_4$ was used as the organic-inorganic-hybrid perovskite. Here, the used $(CH_3NH_3)_2Pb_xSn_{1-x}Cl_4$ was prepared by mixing $CH_3NH_3Cl$ with $Pb_xSn_{1-x}Cl_2$ at a ratio of 2:1.

Here, the luminescence spectrum of the formed organic-inorganic-hybrid perovskite nanocrystalline particle is located between 400 nm and 460 nm.

Manufacturing Example 16

The same process according to Manufacturing Example 1 was performed, and $(C_4H_9NH_3)PbBr_4$ was used as the organic-inorganic-hybrid perovskite. Here, the used $(C_4H_9NH_3)PbBr_4$ was prepared by mixing $(C_4H_9NH_3)Br$ with $PbBr_2$ at a ratio of 2:1.

Here, the luminescence spectrum of the formed organic-inorganic-hybrid perovskite nanocrystalline particle is located at about 411 nm.

Manufacturing Example 17

The same process according to Manufacturing Example 1 was performed, and $(C_5H_{11}NH_3)PbBr_4$ was used as the organic-inorganic-hybrid perovskite. Here, the used $(C_5H_{11}NH_3)PbBr_4$ was prepared by mixing $(C_5H_{11}NH_3)Br$ with $PbBr_2$ at a ratio of 2:1.

Here, the luminescence spectrum of the formed organic-inorganic-hybrid perovskite nanocrystalline particle is located at about 405 nm.

Manufacturing Example 18

The same process according to Manufacturing Example 1 was performed, and $(C_7H_{15}NH_3)PbBr_4$ was used as the organic-inorganic-hybrid perovskite. Here, the used $(C_7H_{15}NH_3)PbBr_4$ was prepared by mixing $(C_7H_{15}NH_3)Br$ with $PbBr_2$ at a ratio of 2:1.

Here, the luminescence spectrum of the formed organic-inorganic-hybrid perovskite nanocrystalline particle is located at about 401 nm.

Manufacturing Example 19

The same process according to Manufacturing Example 1 was performed, and $(C_{12}H_{25}NH_3)PbBr_4$ was used as the organic-inorganic-hybrid perovskite. Here, the used $(C_{12}H_{25}NH_3)PbBr_4$ was prepared by mixing $(C_{12}H_{25}NH_3)Br$ with $PbBr_2$ at a ratio of 2:1.

Here, the luminescence spectrum of the formed organic-inorganic-hybrid perovskite nanocrystalline particle is located at about 388 nm.

Manufacturing Example 20

A light emitting device according to an embodiment of the present invention was manufactured.

First, after an ITO substrate (a glass substrate coated with an ITO anode) is performed, PEDOT: PSS (AI4083 from Heraeus company) that is a conductive material was spin-coated on the ITO anode and then thermally treated for 30 minutes at a temperature of 150° C. to form a hole injection layer having a thickness of 40 nm.

The solution in which the organic-inorganic-hybrid perovskite nanocrystal particle light-emitter according to Manufacturing Example 1 was spin-coated on the hole injection layer and then thermally treated for 20 minutes at a temperature of 80° C. to form an organic-inorganic-hybrid perovskite nanocrystal particle light emitting layer.

Thereafter, 1,3,5-Tris(1-phenyl-1H-benzimidazol-2-yl) benzene (TPBI) having a thickness of 50 nm was deposited on the organic-inorganic-hybrid perovskite nanocrystal particle light emitting layer under a high vacuum state of $1\times10^{-7}$ Torr or more to form an electron transport layer, and then, LiF having a thickness of 1 nm was deposited on the electron transport layer to form an electron injection layer. Then, aluminum having a thickness of 100 nm was deposited on the electron injection layer to form a cathode, thereby manufacturing an organic-inorganic-hybrid perovskite nanocrystal particle light emitting device.

Comparative Example 1

$(CH_3NH_3)_2PbBr_4$ was dissolved in dimethylformamide that is a polar solvent to manufacture a first solution.

Then, the first solution was spin-coated on a glass substrate to manufacture a $(CH_3NH_3)_2PbBr_4$ thin film (OIP film).

Comparative Example 2

$(CH_3NH_3)_2PbCl_4$ was dissolved in dimethylformamide that is a polar solvent to manufacture a first solution.

Then, the first solution was spin-coated on a glass substrate to manufacture a $(CH_3NH_3)_2PbCl_4$ thin film (OIP film).

FIG. 4 is a schematic view of the organic-inorganic-hybrid perovskite nanocrystal having the 2D structure, which is manufactured through an inverse nano-emulsion method according to the present invention.

Referring to 4(a), an organic-inorganic-hybrid perovskite nanocrystal ($ABX_3$) having a 3D, which is formed by using AX and $BX_2$ having a composition ratio of 1:1 as the perovskite materials used in the first solution is illustrated. Here, the A is organic ammonium, the B is a metal material, and the X is halogen. Thus, as illustrated in FIG. 4(a), since the organic material and the inorganic material are not distinguished from each other as a layer and thus organic-inorganic-hybrid perovskite nanocrystals have a 3D structure.

Referring to 4(b), an organic-inorganic-hybrid perovskite nanocrystal ($A_2BX_4$) having a 2D, which is formed by using AX and $BX_2$ having a composition ratio of 2:1 as the perovskite materials used in the first solution is illustrated. As illustrated in the drawings, it is seen that the nanocrystal has a substantially 2D structure because a distance between an inorganic plane and an adjacent inorganic plane increases. Thus, when having the 2D structure, the distance between the organic material and the inorganic material increases to secure the confinement of the inorganic material, and thus, to improve luminescence efficiency due to the improved exciton confinement.

A composition ratio of the perovskite material used in the first solution, e.g., a ratio of AX and $BX_2$ may be adjusted to adjust a bandgap of the organic-inorganic-hybrid perovskite nanocrystal particle.

In the nanocrystal particle light-emitters that have the 2D organic-inorganic-hybrid perovskite nanocrystal structure, the organic-inorganic-hybrid perovskite nanocrystal having the crystal structure, in which the FCC and the BCC are combined with each other, may be formed in the nanocrystal particle light-emitter to form a lamellar structure in which the organic plane and the inorganic plate are alternately stacked, and also, the excitons may be confined in the inorganic plane to implement the high color purity.

Also, the exciton diffusion length may be reduced, and the exciton binding energy may increase in the nanocrystal having a size of 900 nm or less to prevent the excitons from being annihilated by thermal ionization and the delocalization of the charge carriers, thereby luminescence efficiency at room temperature is improved.

Also, the bandgap energy of the organic-inorganic-hybrid perovskite nanocrystal particle may be determined by the crystal structure without depending on the particle size.

Furthermore, since the 2D organic-inorganic-hybrid perovskite is synthesized into the nanocrystal when compared to the 3D organic-inorganic-hybrid perovskite, the exciton binding energy may be increased to further improve the luminescence efficiency and the durability (or stability).

Also, according to the method for manufacturing the organic-inorganic-hybrid perovskite nanocrystal particle light-emitter according to the present invention, the size of organic-inorganic-hybrid perovskite nanocrystal particle light-emitter is adjusted according to the length and size of the alkyl halide surfactant.

It should be noted that the embodiments of the present invention disclosed in the present specification and drawings are only illustrative of specific examples for the purpose of understanding and are not intended to limit the scope of the present invention. It is to be understood by those skilled in the art that other modifications based on the technical idea of the present invention are possible in addition to the embodiments disclosed herein.

DESCRIPTION OF SYMBOLS

100: Organic-inorganic-hybrid perovskite nanocrystal particle light-emitter
110: Organic-inorganic-hybrid perovskite nanocrystal structure
120: Organic ligand

The invention claimed is:

1. An organic-inorganic-hybrid perovskite nanocrystal particle light-emitter, which has a two dimensional (2D) structure, comprising an organic-inorganic-hybrid perovskite nanocrystal structure, is capable of being dispersible in an organic solvent and has a 2D structure.

2. The organic-inorganic-hybrid perovskite nanocrystal particle light-emitter of claim 1, wherein the organic solvent comprises a polar solvent and a non-polar solvent,
the polar solvent comprises dimethylformamide, gamma butyrolactone, N-methylpyrrolidone, dimethylsulfoxide or isopropyl alcohol, and
the non-polar solvent comprises dichloroethylene, trichlorethylene, chloroform, chlorobenzene, dichlorobenzene, styrene, xylene, toluene, or cyclohexene.

3. The organic-inorganic-hybrid perovskite nanocrystal particle light-emitter of claim 1, wherein the 2D structure is an organic-inorganic-hybrid perovskite nanocrystal structure with a center metal centered in a face centered cubic, in which six inorganic halide materials X are respectively located on all surfaces of a hexahedron, and in a body centered cubic, in which eight organic ammonium or inorganic cation are respectively located at all vertexes of a hexahedron and is defined as a structure of which a horizontal length and a vertical length are the same, but a height length is longer by 1.5 times or more than each of the horizontal length and the vertical length.

4. The organic-inorganic-hybrid perovskite nanocrystal particle light-emitter of claim 1, wherein the nanocrystal particle has a spherical, cylindrical, cylindroid, polyprism or 2D shape.

5. The organic-inorganic-hybrid perovskite nanocrystal particle light-emitter of claim 1, wherein the nanocrystal particle has a size of 1 nm to 900 nm.

6. The organic-inorganic-hybrid perovskite nanocrystal particle light-emitter of claim 1, wherein the nanocrystal particle light-emitter has an emission wavelength of 200 nm to 1300 nm.

7. The organic-inorganic-hybrid perovskite nanocrystal particle light-emitter of claim 1, wherein the organic-inorganic-hybrid perovskite nanocrystal particle has bandgap energy determined by the crystal structure without depending on the particle size.

8. The organic-inorganic-hybrid perovskite nanocrystal particle light-emitter of claim 1, wherein the nanocrystal particle has bandgap energy of 1 eV to 5 eV.

9. The organic-inorganic-hybrid perovskite nanocrystal particle light-emitter of claim 1, wherein the organic-inorganic-hybrid perovskite has a structure of $A_2BX_4$, $ABX_4$, or $A_{n-1}BnX_{3n+1}$ (where n is an integer between 2 to 6), and
the A is organic ammonium or inorganic cation, the B is a metal material, the X is a halogen element.

10. The organic-inorganic-hybrid perovskite nanocrystal particle light-emitter of claim 9, wherein the A is $(CH_3NH_3)_n$, $((C_xH_{2x+1})_nNH_3)_2(CH_3NH_3)_n$, $(RNH_3)_2$, $(C_nH_{2n+1}NH_3)_2$, $CF_3NH_3$, $(CF_3NH_3)_n$, $((C_xF_{2x+1})_nNH_3)_2$ $(CF_3NH_3)_n$, $((C_xF_{2x+1})_nNH_3)_2)$, $(CH(NH_2)_2)$, $C_xH_{2x+1}(C(NH_2)_2)$, Cs, Rb, K, $(C_nF_{2n+1}NH_3)_2$ or a combination thereof (where n is an integer equal to or greater than 1, and x is an integer equal to or greater than 1),
the B is a divalent transition metal, a rare earth metal, an alkali earth metal, Pb, Sn, Ge, Ga, In, Al, Sb, Bi, Po, or a combination thereof, and
the X is Cl, Br, I, or a combination thereof.

11. The organic-inorganic-hybrid perovskite nanocrystal particle light-emitter of claim 1, further comprising a plurality of organic ligands surrounding a surface of the organic-inorganic-hybrid perovskite nanocrystal particle.

12. The organic-inorganic-hybrid perovskite nanocrystal particle light-emitter of claim 11, wherein each of the organic ligands has a 2D structure comprising alkyl halide.

13. The organic-inorganic-hybrid perovskite nanocrystal particle light-emitter of claim 12, wherein an alkyl structure of the alkyl halide comprises acyclic alkyl having a structure of $C_nH_{2n+1}$, primary alcohol, secondary alcohol, tertiary alcohol, alkylamine, p-substituted aniline, phenyl ammonium, or fluorine ammonium.

14. A light emitting device comprising:
a first electrode;
a second electrode; and
a light emitting layer disposed between the first electrode and the second electrode and comprising the organic-inorganic-hybrid perovskite nanocrystal particle light-emitter of claim 1.

15. A method for manufacturing an organic-inorganic-hybrid perovskite nanocrystal particle light-emitter having a 2D structure, the method comprising steps of:
preparing a first solution in which organic-inorganic-hybrid perovskite having a 2D structure is dissolved in a polar solvent and a second solution in which an alkyl halide surfactant is dissolved in a non-polar solvent; and
mixing the first solution with the second solution to form the nanocrystal particle.

16. The method of claim 15, wherein the step of mixing the first solution with the second solution comprises a step of dropping the first solution dropwise into the second solution to mix the first and second solutions with each other.

17. The method of claim 15, wherein the organic-inorganic-hybrid perovskite has a structure of $A_2BX_4$, $ABX_4$, or $A_{n-1}BnX_{3n+1}$ (where n is an integer between 2 to 6), and
the A is organic ammonium or metal cation, the B is a metal material, the X is a halogen element.

18. The method of claim 17, wherein the A is $(CH_3NH_3)_n$, $((C_xH_{2x+1})_nNH_3)_2(CH_3NH_3)_n$, $(RNH_3)_2$, $(C_nH_{2n+1}NH_3)_2$, $CF_3NH_3$, $(CF_3NH_3)_n$, $((C_xF_{2x+1})_nNH_3)_2(CF_3NH_3)_n$, $((C_xF_{2x+1})_nNH_3)_2)$, $(CH(NH_2)_2)$, $C_xH_{2x+1}(C(NH_2)_2)$, Cs, Rb, K, $(C_nF_{2n+1}NH_3)_2$ or a combination thereof (where n is an integer equal to or greater than 1, and x is an integer equal to or greater than 1),
the B is a divalent transition metal, a rare earth metal, an alkali earth metal, Pb, Sn, Ge, Ga, In, Al, Sb, Bi, Po, or a combination thereof, and
the X is Cl, Br, I, or a combination thereof.

19. The method of claim 17, wherein the first solution is formed by mixing AX and $BX_2$ with the polar solvent at a predetermined ratio.

* * * * *